United States Patent
Rinaldo et al.

(10) Patent No.: US 11,481,701 B2
(45) Date of Patent: Oct. 25, 2022

(54) COMPUTER-BASED DYNAMIC DATA ANALYSIS

(71) Applicant: Mayo Foundation for Medical Education and Research, Rochester, MN (US)

(72) Inventors: Piero Rinaldo, Rochester, MN (US); David M McHugh, Rochester, MN (US); Gregg Marquardt, Rochester, MN (US); Neil Maffitt, Rochester, MN (US); Robert J. Currier, San Fransisco, CA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 828 days.

(21) Appl. No.: 14/440,827

(22) PCT Filed: Nov. 5, 2013

(86) PCT No.: PCT/US2013/068535
§ 371 (c)(1),
(2) Date: May 5, 2015

(87) PCT Pub. No.: WO2014/071384
PCT Pub. Date: May 8, 2014

(65) Prior Publication Data
US 2015/0294075 A1    Oct. 15, 2015

Related U.S. Application Data

(60) Provisional application No. 61/722,761, filed on Nov. 5, 2012.

(51) Int. Cl.
*G16H 50/70* (2018.01)
*G16H 10/40* (2018.01)
(Continued)

(52) U.S. Cl.
CPC .......... *G06Q 10/063* (2013.01); *G16H 10/40* (2018.01); *G16H 40/67* (2018.01); *G16H 50/20* (2018.01); *G16H 50/30* (2018.01); *G16H 50/70* (2018.01)

(58) Field of Classification Search
CPC .. G06F 19/3418; G06F 19/328; G06F 19/322; G06F 19/3487; G06F 2216/03;
(Continued)

(56) References Cited

U.S. PATENT DOCUMENTS

2003/0233250 A1*  12/2003  Joffe ................. G16H 15/00
                                                      705/2
2005/0119534 A1*  6/2005  Trost .................. G16H 50/30
                                                      128/920

(Continued)

OTHER PUBLICATIONS

Gregg Marquardt, MSS, et al.; "Enhanced interpretation of newborn screening results without analyte cutoff values"; Jul. 2012; American College of Medical Genetics and Genomics, *Genetics in Medicine*, vol. 14, No. 7, pp. 648-655.*

(Continued)

*Primary Examiner* — Evangeline Barr
(74) *Attorney, Agent, or Firm* — Fish & Richardson P.C.

(57) ABSTRACT

A computer-implemented method comprises storing data that aggregates statuses, uploaded by healthcare providers, of a plurality of patients for a plurality of medical conditions; receiving via a remote upload from a healthcare provider data that characterizes the status of the particular patient with respect to at least some of the plurality of medical conditions; providing for review by the healthcare provider data that graphs a plotted location that is indicative of the particular patient's values in a common graph with locations that are indicative of the other patients' values, and that highlights the particular patient's values relative to the (Continued)

other patients' values; and adding data for conditions of the particular patient to a database that aggregates the statuses of the plurality of patients.

17 Claims, 11 Drawing Sheets

(51) Int. Cl.
*G16H 50/20* (2018.01)
*G16H 50/30* (2018.01)
*G16H 40/67* (2018.01)
*G06Q 10/06* (2012.01)

(58) Field of Classification Search
CPC ........ G16H 40/40; G16H 40/60; G16H 40/67; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/63; G16H 50/00; G16H 70/00; G16H 70/20; G16H 70/40; G16H 70/60; G16H 80/00; G06Q 50/24; G06Q 40/08
See application file for complete search history.

(56) References Cited

U.S. PATENT DOCUMENTS

| | | | | |
|---|---|---|---|---|
| 2006/0136263 | A1* | 6/2006 | Fry | G06Q 10/10 705/2 |
| 2008/0009684 | A1* | 1/2008 | Corsetti | A61B 5/00 600/300 |

OTHER PUBLICATIONS

Marquardt et al., "Enhanced interpretation of newborn screening results without analyte cutoff values," Genet Med., 14(7):648-655, Epub Feb. 16, 2012.

McHugh et al., "Clinical validation of cutoff target ranges in newborn screening of metabolic disorders by tandem mass spectrometry: a worldwide collaborative project," Genet Med., 13(3):230-254, Mar. 2011.

International Search Report and Written Opinion for PCT/US2013/068535, dated Mar. 20, 2014, 7 pages.

International Preliminary Report on Patentability for PCT/US2013/068535, dated May 14, 2015, 6 pages.

\* cited by examiner

MS/MS COLLABORATIVE PROJECT

Region4 Genetics Collaborative

| Home | Data Submission | Tools & Report | User Settings | Documentation | Site Admin | Log Out |

Welcome: Piero Rinaldo

Select A Tool

● Released    ○ Not Released

Type             Condition           Tool Type    Tool
[Amino Acid ▶]  [All Conditions ▶]  [Single ▶]  [PC 001 2012-09-25 [Single] ▶]  [Add]

○ Run Selected Tools  ☐ Show Non-Informative Scores
● Run All Single Tools    Results to Excel
                          [None ▶]

Tools Selected to Run

No Tools Selected

Select Data File

File Format: [Standard Format [D] ▶]  [Choose File] 20121029213..._LOINC.csv  Override Start Row: [    ]  End Row: [    ]  [Run Tools]

FIG. 4B

Case Count: 56    Run Count (Tools* Cases): 2464

File Name: 20121029213420_LOINV.csv

Batch ID: S:\SNS 2012YA\October 2012\SNS20121029202YA_317992.wiff

[ + ] Informative Results

Case ID: 39   All Conditions Tool

| Percentile | Tool | Guideline |
|---|---|---|
| 79 | MET 012 2012-06-20 [Single] | Condition is very likely MET. (Score of 294 >= 100) |
| 92 | TPN-I 005 2011-12-30 [Single] | Condition is very likely TPN. (Score of 151 >= 55) |

Case ID: 48   All Conditions Tool

| Percentile | Tool | Guideline |
|---|---|---|
| 3 | CPT-I 008 2011-12-31 [Single] | Condition is possibly CPT-I. (Score of 30>= AND <70) |

Case ID: 52   All Conditions Tool

| Percentile | Tool | Guideline |
|---|---|---|
| 40 | TPN 005 2011-12-30 [Single] | Condition is very likely TPN. (Score of 73 >=55) |

Case ID: 53   All Conditions Tool

| Percentile | Tool | Guideline |
|---|---|---|
| 3 | TPN 005 2011-12-30 [Single] | Condition is possibly TPN. (Score of 21 >=20 AND < 40) |

Case ID: 54   All Conditions Tool

| Percentile | Tool | Guideline |
|---|---|---|
| 28 | 2MBG 004 2012-01-02 [Single] | Condition is very likely 2MBG. (Score of 55 >=50) |

FIG. 4C

MS/MS COLLABORATIVE PROJECT

Post-Analytical Tool
2MBG 004 2012-01-02 [Single]

Printed Cnc: 11/2/2012 9:50 AM  Participant: Minnesota
Tool Last Modified: 1/2/2012 11:06 AM  Printed By: Piero Rinaldo

Cumulative Normal Percentage & 2MBG Disease Range Overlap Values

| Analyte | Normal | Overlap | Disease Range | | | | Case Values |
|---|---|---|---|---|---|---|---|
| C3 | 4.57 | 91.9% | 0.69 | 0.93 | 1.13 | 2.29 | 0.41 |
| Met | 41.53 | 92.1% | 11.94 | 15.15 | 17.76 | 26.09 | 23.17 |
| C2 | 51.04 | 96.7% | 9.53 | 12.89 | 13.98 | 23.00 | 9.85 |
| C0 | 57.77 | 97.2% | 10.72 | 13.64 | 16.28 | 25.65 | 16.30 |
| Phe | 95.89 | 97.4% | 28.00 | 35.45 | 40.10 | 58.99 | 51.10 |
| Xle | 239.69 | 98.0% | 66.86 | 73.17 | 80.16 | 114.52 | 156.47 |
| C8:1 | 0.28 | 99.8% | 0.02 | 0.03 | 0.094 | 0.08 | 0.08 |
| Val | 219.55 | 100.3% | 46.88 | 54.01 | 57.64 | 83.54 | 147.12 |
|  | 99%ile | %ile | 1%ile | 5%ile | 10%ile | 50%ile | Values |
| C5 | 0.39 | 0.0% | 0.51 | 0.55 | 0.56 | 0.33 | 0.40 |
| C5/C0 | 0.02 | 9.7% | 0.01 | 0.02 | 0.02 | 0.00 | 0.02 |
| C5/C2 | 0.02 | 17.0% | 0.01 | 0.02 | 0.02 | 0.00 | 0.04 |
| C5/C3 | 0.33 | 50.8% | 0.12 | 0.15 | 0.18 | 0.22 | 0.98 |

☐ NP – DR Overlap

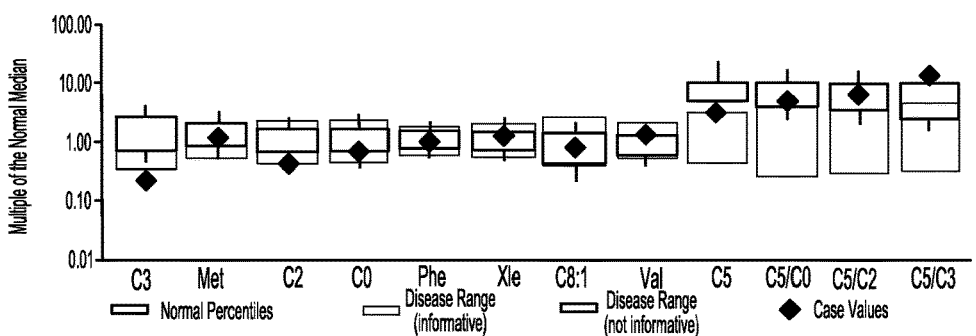

Case Score

| 55 | 46 | 59 |
|---|---|---|
| All | United States | Minnesota |

View Calculations

File Rank of all 2MBG

| 28% | 19% | 29% |
|---|---|---|
| All | United States | Minnesota |

Count of 2MBG Scores

| 84 | 85 | 66 |
|---|---|---|
| All | United States | Minnesota |

Score Interpretation Guidelines

The tool has been validated only for neonatal (<10 days) blood spots. Use of the tool is not advised to calculate scores for older patients.

Score is >=50
condition is very likely 2 MBG

Score is >=30 and <50
condition is likely 2 MBG

Score is >=10 and <30
condition is possibly 2 MBG

Score is < 10
Profile is not informative

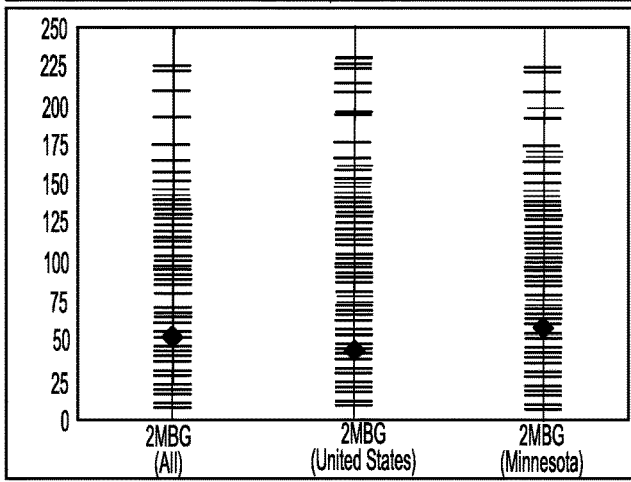

FIG. 4E

COMPUTER-BASED DYNAMIC DATA ANALYSIS

CROSS-REFERENCE TO RELATED APPLICATIONS

This application is a National Stage application under 35 U.S.C. § 371 of International Application No. PCT/US2013/068535, having and International Filing Date of Nov. 2, 2013, which claims the benefit of U.S. Provisional Application Ser. No. 61/722,761, filed Nov. 5, 2012. The disclosure of the prior applications are considered part of (and are incorporated by reference in) the disclosure of this application.

STATEMENT AS TO FEDERALLY SPONSORED RESEARCH

This invention was made with government support under HHSN275201000017C and HHSN275200800001C awarded by the National Institutes of Health. The government has certain rights in the invention.

TECHNICAL FIELD

This document relates to computer-implemented up-to-date, on demand, and real time interpretation of profiles of laboratory results, using a web-based application provided by a central computer server system, to diagnose patients with one of several conditions by comparison with condition ranges established from other patients known to be affected (true positives) according to clinical presentation, family history and genotyping, and response to treatment.

BACKGROUND

In modern medicine, the diagnosis of a patient's condition is increasingly dependent on the integration of multiple laboratory results. Typically, these laboratory tests are developed and validated according to standard procedures that include the selection of cut-off values that reflect enough deviation from the reference population to indicate that the result should be considered abnormal. A common challenge for an ordering physician is how to react to a random "abnormal" result that does not fit the overall pattern. Some physicians may have the experience to overrule such a result, but most physicians take a prudent approach and order additional tests, often the beginning of an unnecessary and expensive cycle.

This type of situation is particularly common with respect to the evaluation of a patient suspected to have a defect in his/her genetic make-up. For example, a diverse array of specimens (for example urine, blood, CSF, tissues biopsies) can be taken from a patient and can be tested to identify the presence of characteristic, yet highly complex phenotypes. The level at which such testing indicates the presence of a marker can be binary (i.e., the patient has a mutation or does not) or analog (i.e., the level of either a gene product or of a downstream metabolite can vary based on a variety of factors, and that variability can be reflected in the test results). And again, professionals in laboratory medicine may select certain cut-off levels that represent a statistical threshold of likelihood of disease.

SUMMARY

This document describes systems and techniques that may be used to provide an integrated interpretation (expressed as a score) of multiple laboratory results obtained during an episode of care about a patient vis-à-vis other patients who have previously been enrolled with a system. The systems described here provide an evolving process of clinical validation, and continue to improve over time with every addition of new knowledge (e.g., the addition of test data from a new patient, or additional data for an existing patient). Such a score may be used by a physician to understand where the patient under evaluation ranks among patients known to be affected by the condition.

In the case of genetic and multifactorial conditions, the elements that lead to the diagnosis of a certain medical condition can be very complex and multi-dimensional. As a result, a physician can also use multi-condition comparison tools embedded in systems described below that allow the physician to narrow down the differential diagnosis to two conditions, and have a plot made of those conditions relative to each other. For example, the positions of patients (e.g., as indicated by their cumulative scores calculated by two tools) may be plotted on the X and Y axis of a scatter plot for condition A and condition B, respectively. Such a scatter plot determines if the patient under consideration falls within either of the condition clusters.

Such systems and methods may, in particular implementations, provide one or more advantages. For example, a physician can be presented with an indication of where a particular patient sits relative to an entire corpus of other patients with respect to a condition, rather than (or in addition to) where the patient sits with respect to an absolute cut-off point established to reflect segregation from a reference population. As a result, the physician may be provided additional information, and may better use his or her judgment in diagnosing the patient. Also, the data reflected by a system may be constantly updated, because the range of "other" patients changes every time a new patient is added to the database.

In one implementation, a computer-implemented method for identifying a status of a particular patient with respect to one or more medical conditions is disclosed. The method comprises storing at a computer system data that aggregates statuses of a plurality of patients other than the particular patient with respect to a plurality of medical conditions; receiving, at the computer system, data that characterizes the status of the particular patient with respect to one or more of the plurality of medical conditions; comparing the data that characterizes the particular patient to the data that aggregates statuses of the plurality of patients, to generate for each of one or more conditions of the plurality of conditions, a score for the particular patient that indicates the particular patient's relative position in comparison to the plurality of patients other than the particular patient; and providing, over a computer network and for review by a registered user of the computer system, data that shows multiple scores for the particular patient for each of multiple different medical conditions. The data that aggregates statuses of the plurality of patients can be analyzed using multivariate pattern recognition techniques. Also, the score can be represented as a percentile rank of the particular patient in relation to the scores from patients known to have the condition (true positives). In some aspects, the score is a parameter-less number and can additionally be a percentile. In other aspects, the condition can be expressed by data from laboratory markers.

In certain aspects, the condition is expressed as a value along a range of values, and the score is expressed as a percentile of a value for the particular patient as compared to values for the other patients. Also, the data provided for review can comprise data that shows correlation between two different conditions, including data that expresses the particular patient's position with respect to the two conditions. Moreover, the data can be formatted to present a scatter plot that shows positions of the particular patient among the other patients for the two conditions, wherein each axis of the scatter plot represents the likelihood of having the conditions. Also, the method can additionally include receiving data from the registered user of the computer system, the data defining a tool for analyzing and expressing relative positions of patients with respect to a particular condition. In addition, the method may further comprise identifying that an administrator of the computer system has indicated that the tool is approved, and in response, making the tool available to other registered users of the computer system.

In yet other aspects, the method further comprises electronically correlating documents that discuss a particular condition with one or more tools for evaluating a patient's position relative to other patients for the condition, such that a registered user evaluating the particular patient can click to be presented with one or more of the documents. In addition, the method can include checking the received data at the time it is uploaded to confirm that the received data is within acceptable ranges defined by the system. And further, the providing of data that shows the multiple scores for the particular patient for each of multiple different medical conditions can comprise identifying which conditions, of the plurality of conditions, are capable of being identified for the particular patient based on identifying analytes provided for the particular patient to the system.

Other features and advantages will be apparent from the description and drawings, and from the claims.

DESCRIPTION OF DRAWINGS

FIG. 4B is a screen shot of an interface for selecting files containing patient data for post-analytical interpretation.

FIG. 4C is a screen shot showing a summary of an import of a file containing patient data (56 cases analyzed, 2464 scores calculated, 6 informative scores).

FIG. 4E is a screen shot of a reporting tool for one patient condition.

DETAILED DESCRIPTION

Figure 1:
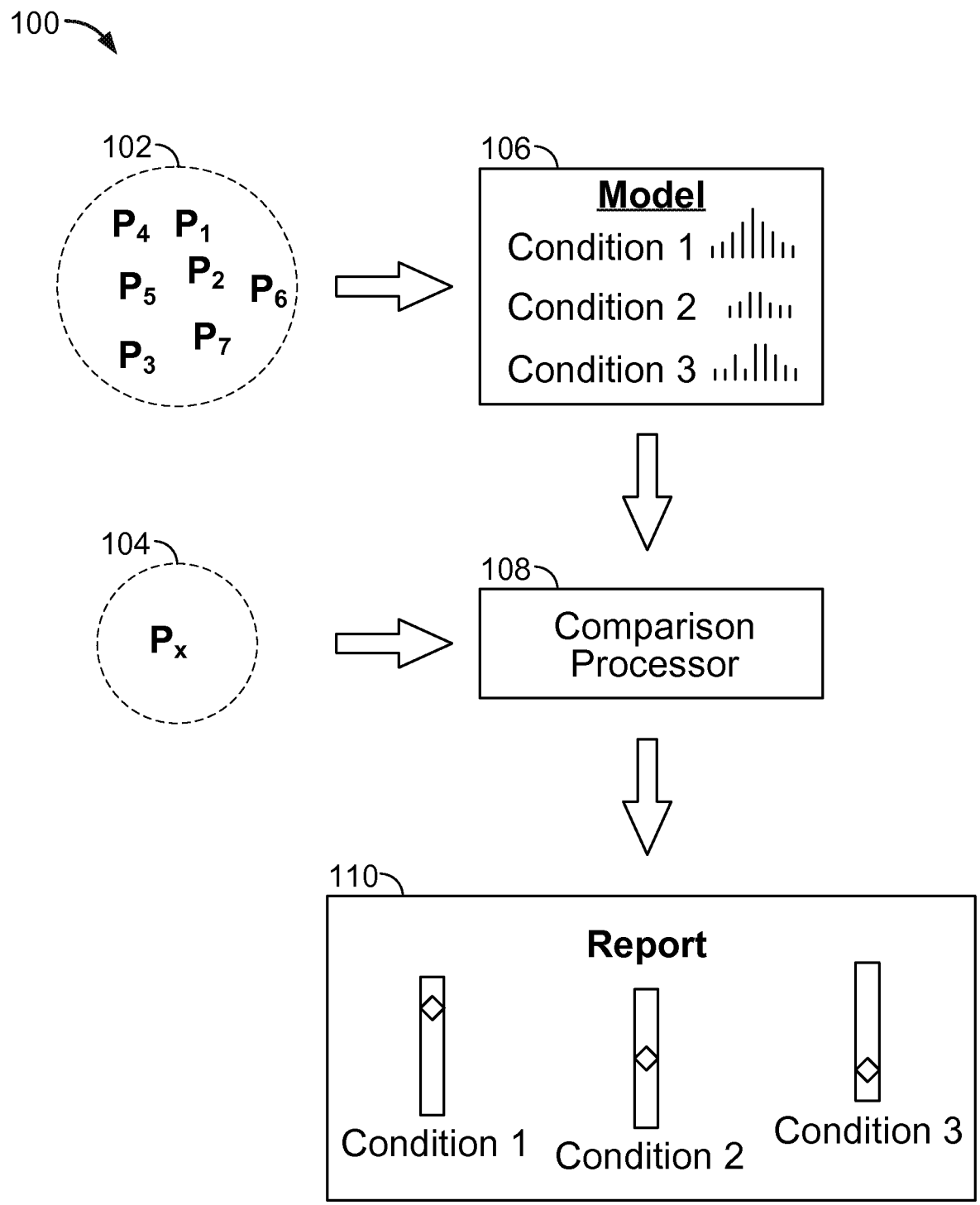
FIG. 1 is schematic diagram showing processing of comparative patient data.

In general, this document discusses techniques for processing patient-specific medical data to achieve an integrated post-analytical interpretation of the data. As discussed below, the score for a particular patient can be expressed as a percentile rank relative to scores of other patients confirmed to have the condition under test. This comparative expression of the patient's condition can be beneficial in allowing a physician or other healthcare provider to better appreciate where the particular patient sits vis-à-vis other patients and to make an objective, evidence-based decision about the patient's health or status. For example, the physician may be more efficient and selective in ordering more testing to confirm the diagnosis.

As described here, episodes for care of undiagnosed patients could be very data-intensive and their integrated interpretation is a challenge if performed manually, and time consuming. Rather, a computer system implemented as an internet-connected server system may communicate with a large number of registered users (e.g., physicians or laboratory personnel) and may receive uploads of information about patients for whom such individuals are caring. The quality of new submission can be monitored by a system curator who is a content expert of the conditions and is able to question outlier entries. The central system may anonymize such data (or it may be submitted according to a patient ID with no patient identifying information ever being made available to the central system) and may then store and aggregate it to develop statistical information about particular conditions, and genetic markers or other information that may be correlated to such medical conditions. Such aggregated information may then be used to establish a standard, such as a statistical distribution (percentiles, multiple of the reference median) of individual levels reported for the various patients who have been reported to the system.

Such data representing the statistical distribution may then be used as the reference set when a subsequent patient is enrolled with the system, such as by a laboratory professional uploading data for that patient or a group of patients. The user may then be presented with data that represents the patient's updated position relative to the other patients in the group—for a particular condition (e.g., for a particular market or combination of markers) or a number of different conditions. Such information may then be reported back to a treating physician who may use it to act accordingly with respect to the patient.

As one example, data for a number of parameters may be entered for the patient, and the system may determine which conditions can be reported for the particular patient from the submitted data. A query of all conditions handled by the system (or a sub-set of such conditions) may then be displayed, with notification of any missing data that prevent the evaluation of one or more of the conditions targeted by the system. The patient's score for each condition may be shown as a percentile rank against scores of patients known to have the condition. A user can then enter additional information for the particular patient, and may update such an "all conditions" display, such as by having additional conditions be graphed against the reference population, where the additional data entered by the user permits such a comparison.

In another example, it can be difficult to identify whether a patient has a condition simply by looking at parameters that may be relevant to that one condition, as certain indicators are indicative for multiple different conditions, particularly for patient values that are not extreme. Thus, in the second example, a user can select to plot a patient's data relative to two selected conditions (where the user can explicitly select each such condition or can select pairs of conditions that have previously been placed together in a list). Such a scatter plot can often quickly indicate by visual inspection whether the patient has the first condition, the second condition or neither. Another possible outcome is an inconclusive score, meaning that at the current level of information (number of patients with either condition) it is not yet possible to choose one or the other. This outcome may improve as more confirmed cases are added to the comparison processor 110. By intelligent selection of the conditions to compare (i.e., by understanding how the conditions may relate to each other, either actually or falsely), a physician or other caregiver may be able to resolve the condition that a patient may have, where such resolution may not have been available looking at a single condition alone, or multiple conditions individually.

FIG. 1 is schematic diagram showing processing of comparative patient data. In general, the diagram shows a system 100 by which data from a large plurality of patients is provided to a system, and subsequently, corresponding data for a particular patient is provided, and comparative data that shows the particular patient's position relative to the other patients (represented as a statistical range or distribution) may then be provided to a user, such as the user who provided the data for the particular patient.

Referring now more specifically to components in FIG. 1, a population's data 102 is shown graphically as a group indicated by individual P designations, and an individual's user data 104 by a single P. The patient data may take the form of results from any properly-validated laboratory testing. For example, various healthcare organizations and their respective laboratory systems throughout the world may have taken samples from patients and characterized many classes of markers, such as determinations of either high or low levels of these markers found for particular patients. Such testing may be conducted according to standardized techniques, so as to assure that comparisons between patients are as apples-to-apples as is practical.

Such data may have been uploaded to a system over time, and the system may have used the data to generate a model 106 which is the training set for the comparison processor 108 to define a pattern unique to a determined condition, or disease. The model 106 shows histograms representing reference and condition ranges to represent the fact that data from multiple users is aggregated by the model, and also that statistical representation of such data can be stored and/or easily computed. Such data may be stored in a variety of manners, and may be analyzed at periodic points in time with the results of the analysis stored, or may be analyzed at the time a registered user of the system 100 requests such data, or a combination of both.

User data 104 represents data uploaded by a user who is registered with the system 100, made on behalf of a particular patient (represented by the P in the image). Such data may be for an individual patient, or for multiple patients (e.g., in the form of a .csv or similar file where each record represents data for a different patient). For example, results may be submitted by independent laboratories at the same time, and large number of parallel multivariate pattern-recognition operations may be performed on the submitted data in order to identify clinical relevance of multiple markers—e.g., when the median of a condition range is outside either the upper or the lower percentile limits of a reference population. Such analysis may also be a function of degree of penetration within a respective condition range and proportionally weighted correction factors.

The information for particular patients can simply be uploaded to add to the model 106 and can also be comparatively analyzed against the population's data 102. A comparison processor 108 may perform operations, described in more detail below, to compare certain data 104 for a particular case under investigation, to the corresponding data 102 for the population of true positive cases previously provided to the system 100. For example, a certain value may be represented in the user data 104 for a certain trait, or condition associated with the trait, and the same value may be represented for most or all of the other patients. The system may then relate the particular patient's values to the respective condition ranges and assign scores on the basis of the degree of penetration in the condition range that does not overlap with the reference range.

Figure 4A:
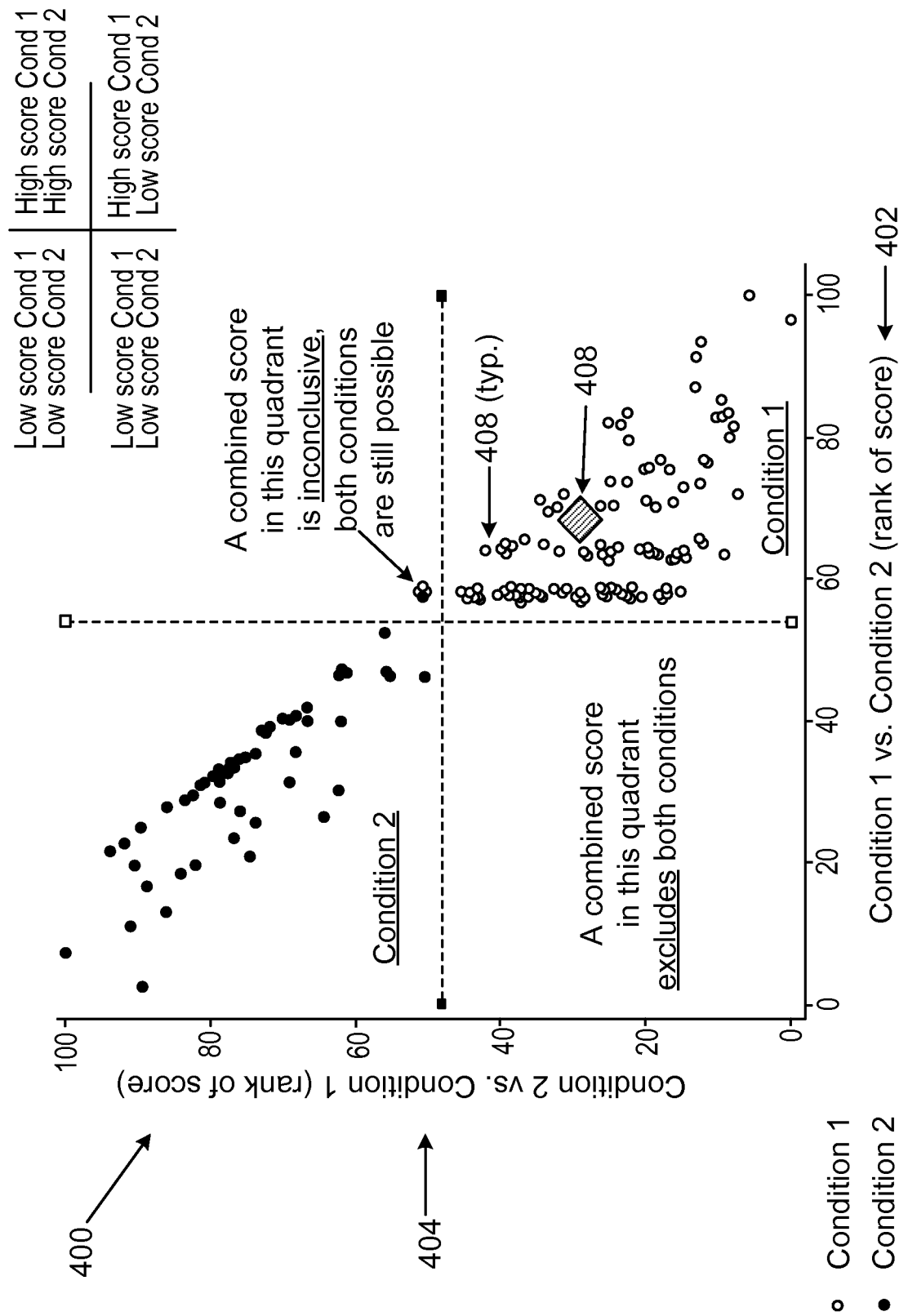
FIG. 4A is a screen shot of an interface for presenting direct comparative analysis for two conditions both with informative single condition scores and therefore representing a challenging differential diagnosis.
Figure 4D:
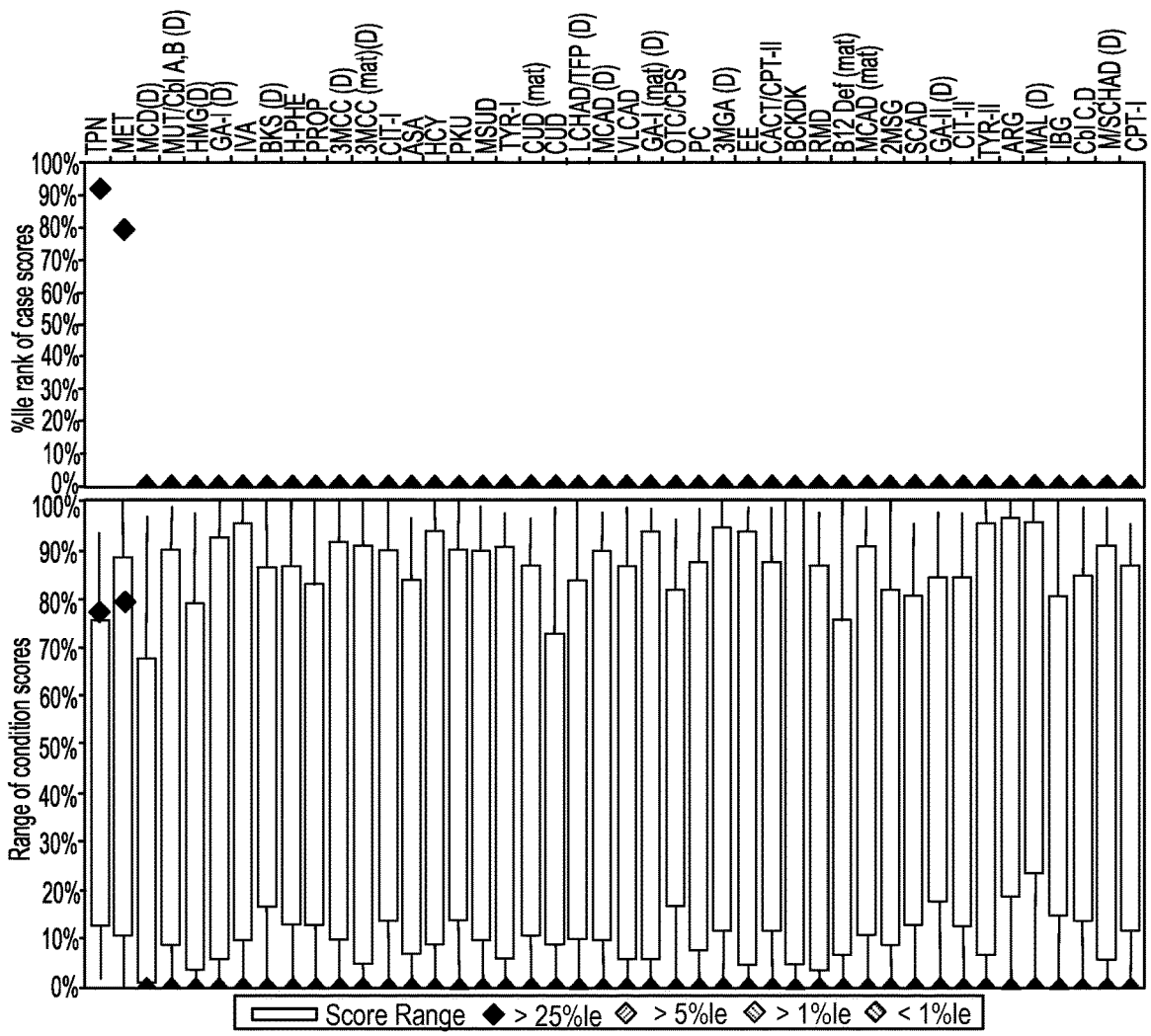
FIG. 4D is a screen shot of a reporting tool for all patient conditions.

The system 100 may then generate a report 110 that displays to a registered user the information determined from the comparison. For example, the sort of comparison just discussed may be repeated for a number of different conditions, and data may be generated for each individually (e.g., as shown in FIGS. 4C-4E). Thus, in a tabular format (FIG. 4C), the system 100 has generated a report that shows any informative score for any condition and the respective ranking For example, for condition 1 (shown as MET in FIG. 4C, case ID: 39), a particular patient may stand at the 79th percentile rank, but also at the 92th percentile rank for condition 2 (shown as TPN in FIG. 4E, case ID: 39). The registered user (e.g., a lab technician) or someone who receives the report 110 from the registered user (e.g., a treating physician) may then interpret this data as they see fit from their level of training. For example, they may determine that the particular patient has a stronger association with condition 2. The system is designed to minimize multiplicity of informative outcome, and it strives to pinpoint the correct condition.

In certain instances, the conditions that are reported on may be a function of the patient information that a user enters. For example, the system 100 may be programmed to recognize that certain analytes, alone or in combination with other analytes, are representative of a patient's susceptibility to a particular condition. Thus, where those analytes are entered for a patient by a registered user, a report for the patient may plot the patient's value relative to the population that is in the database. Where such analytes were not entered by the registered user, the particular location in a report may be left blank.

Additional data may also be provided with the report 110. For example, the labels for each condition may be hyperlinks, and clicking on them may bring the reviewer certain information. As one example, the information may be information that helps the reviewer interpret the data, such as textual explanations or indicators or where the 25th, 50th, and 75th percentiles are located. Alternatively, or in addition, clicking on the link may bring the review to a document (e.g., a web page) that further links to other documents that provide in-depth explanations of the particular selected condition. For example, one report may provide data for all conditions enabled by enough patients and by all required markers in the comparison processor 108 for a patient (see FIG. 4D), and clicking on a designator for one of the conditions may cause the system 100 to display a report for the particular selected condition (see FIG. 4E). Such resources may be used by physicians who are not familiar with the particular condition and need assistance in understanding how it operates, and what the particular test score for the particular user means in terms of the patient's health.

In this manner, the system 100 can obtain data about patient conditions and associations efficiently and can report the data to users who in turn provide additional data to grow the database. Such reports may also be performed efficiently by automatically correlating them to scores of other patients, rather than requiring an expert to identify a particular issue and to determine levels of a particular unit (e.g., a certain number or volume of some factor in test results).

Figure 2:
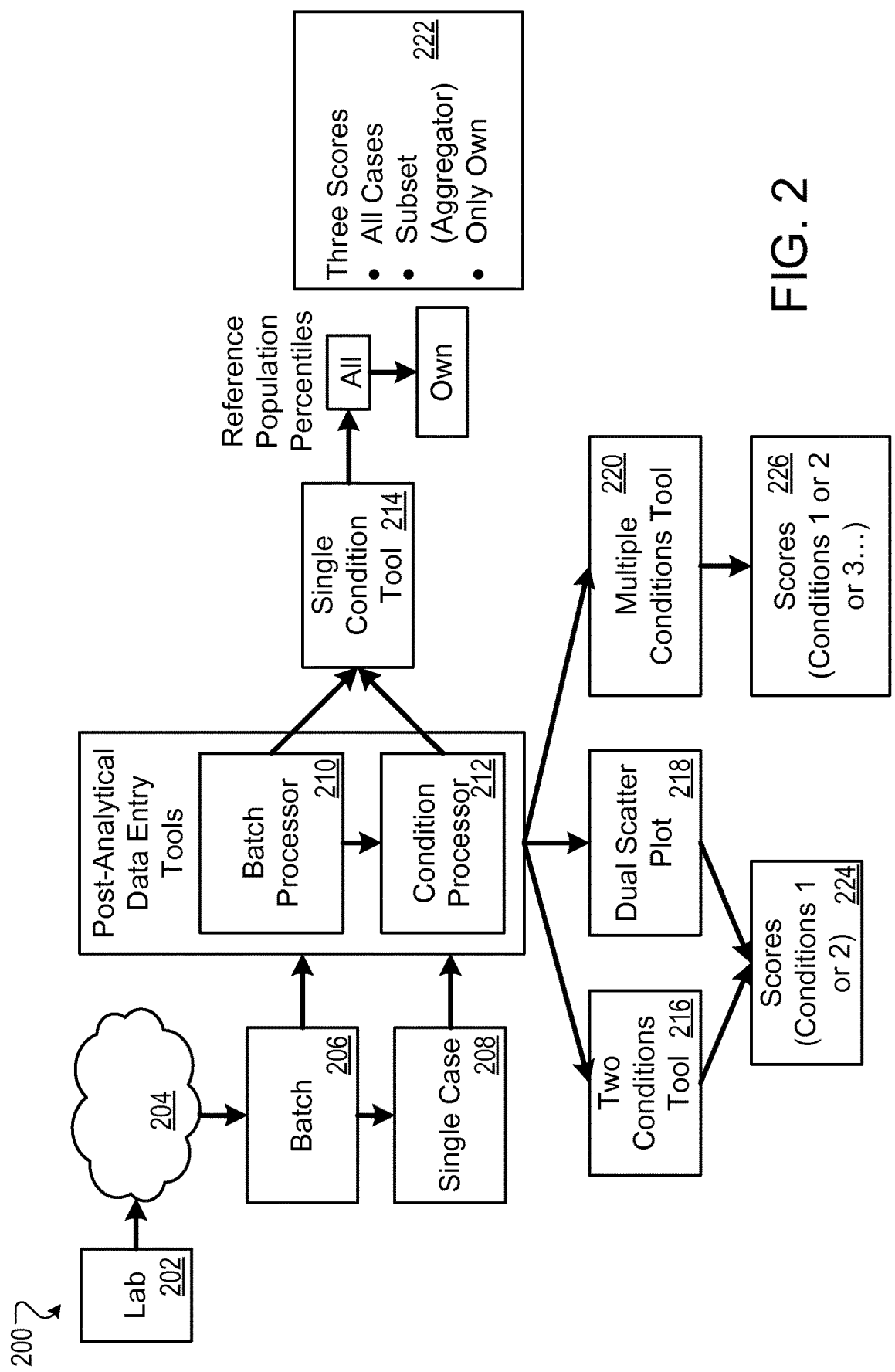
FIG. 2 is a schematic diagram that shows components of a patient comparison system.

FIG. 2 is a schematic diagram that shows components of a patient comparison system 200. The system 200 may be used to carry out processes like those discussed above in FIG. 1 for the system 100. The system 200 comprises structural components at a plurality of labs, and at a central computer server system that handles data acquisition, analysis, aggregation, and comparison for data relating to conditions that patients may exhibit and that others would like to study—either for research or for diagnosing a particular patient.

For example, laboratory 202 represents a computer terminal (e.g., a tablet computer, personal computer, smartphone or the like) operated by an employee of a patient testing facility, such as a laboratory affiliated with a clinic or hospital. The laboratory 202 may connect through a network such as a LAN and/or the internet 204 to the central server system that is represented by the remaining blocks in the system. An interface, such as web front-end, may present mechanisms for batch loading 206 and single case loading 208 of data about patients. Data loading may occur, for example, by the uploading of batched results in the form of a data file, while single case loading 208 may occur by a user at the laboratory 202 filling out a web form or pasting in figures from an laboratory application on the user's computer.

The uploading components 206, 208 may in turn provide the uploaded data to a sub-system that includes a batch processor 210 and condition processor 212, which may respectively break apart batch submissions and assign them identifiers, and process particular ones of single case submissions or entries in a batch submission. The condition processor 212 may, for example, identify various fields in a submission and confirm that they correspond to particular fields in a database of all patient data stored by the central system. In addition, the values of certain parameters may be checked to ensure that they are not outside of predetermined acceptable bounds. If they are, the system 200 may immediately generate a warning message to instruct the user to fix the data or re-upload the data, or may reject the submission of the user does not do so. The condition processor may also perform additional process at upload time, such as by incorporating data about conditions for the just-uploaded patients into aggregated data for a larger population of patients.

Further analysis and statistical manipulation may occur as part of the upload, and additional processing may occur if the user requests reports on the patient or patients whose data has just been uploaded. For example, a single condition module 214 may perform a comparison between a particular patient's data and that of other patients for a particular identified condition. A dual condition module 216 may perform a similar analysis and comparison for two conditions. Each module 214 and 216 may also produce scores and other representations, such as graphs or textual descriptions to express the comparison of the user to the stored group of other users.

A dual scatter plot module 218 may analysis the particular user relative to other users in two or more conditions, where one condition is expressed on one dimension and the other condition is expressed on the other dimension of a graph. The values along the axes can be percentile at which particular patients fall for each such condition. A representation of such a graph is shown in FIG. 4A.

A multiple condition module 220 may operate in manners similar to the dual condition monitor 216, but may extend its analysis to three or more different conditions, and may generate data for a visual representation that is matched to the level of information being analyzed. In general, a user may select the conditions to be displayed in a multiple conditions module 220. Alternatively, the multiple condition module 220 can be implemented in the form of an all conditions module. In such a situation, the system can provide a report of data for all conditions that the system is able to analyze for a particular patient. For example, each condition may be dependent on the presence and weighting of scores for multiple different analytes. Where a user enters data for a patient for all such analytes that lead to the condition score, the system may report such a score, and for other conditions, may not report a score.

The various modules may be used to analyze and generate output data that a computer system or user may review. For computer review, numerical scores and other data may be generated according to an application programming interface (API) that is known to member labs and to the central system. The labs may then process such information, such as by automatically routing it to physicians who are identified as treating physicians for the particular patients whose data was analyzed. Such physician-side processing may also format the data for presentation or can provide the data in a manner formatted by the server system (e.g., as HTML or PDF documents).

The presentation processing at the server system can include generation of various scores for each of one or more patients, where the scores do not have units, but instead express the patient's position vis-à-vis other patent's for a particular parameter, generally as a percentile. For example, standard statistical techniques can be used to take a patient's value as an input and to identify the percentile at which the value falls with respect to the values for the same parameter for other patients in a group—including as compared to a sub-group of patients determined to have the particular condition. The scores against which a patient is compared may also be filtered such as by showing how the patient compares to the data for all other patients who have loaded relevant data, all patients in the same country, all patients sharing some characteristic with the particular patient (e.g., age, gender, race, or the like) and other factors. Such a score may be presented as a single score for each such sub-group comparison (box 222).

Other comparisons may include greater than two conditions and may be presented accordingly. For example, a score 224 may be computed for a user against two different conditions, or a score 226 may be computed against more than two conditions. Such comparisons (and associated graphics or other presentations of information) may permit a treating physician or research to resolve overlapping patterns between two different conditions.

Figure 3:
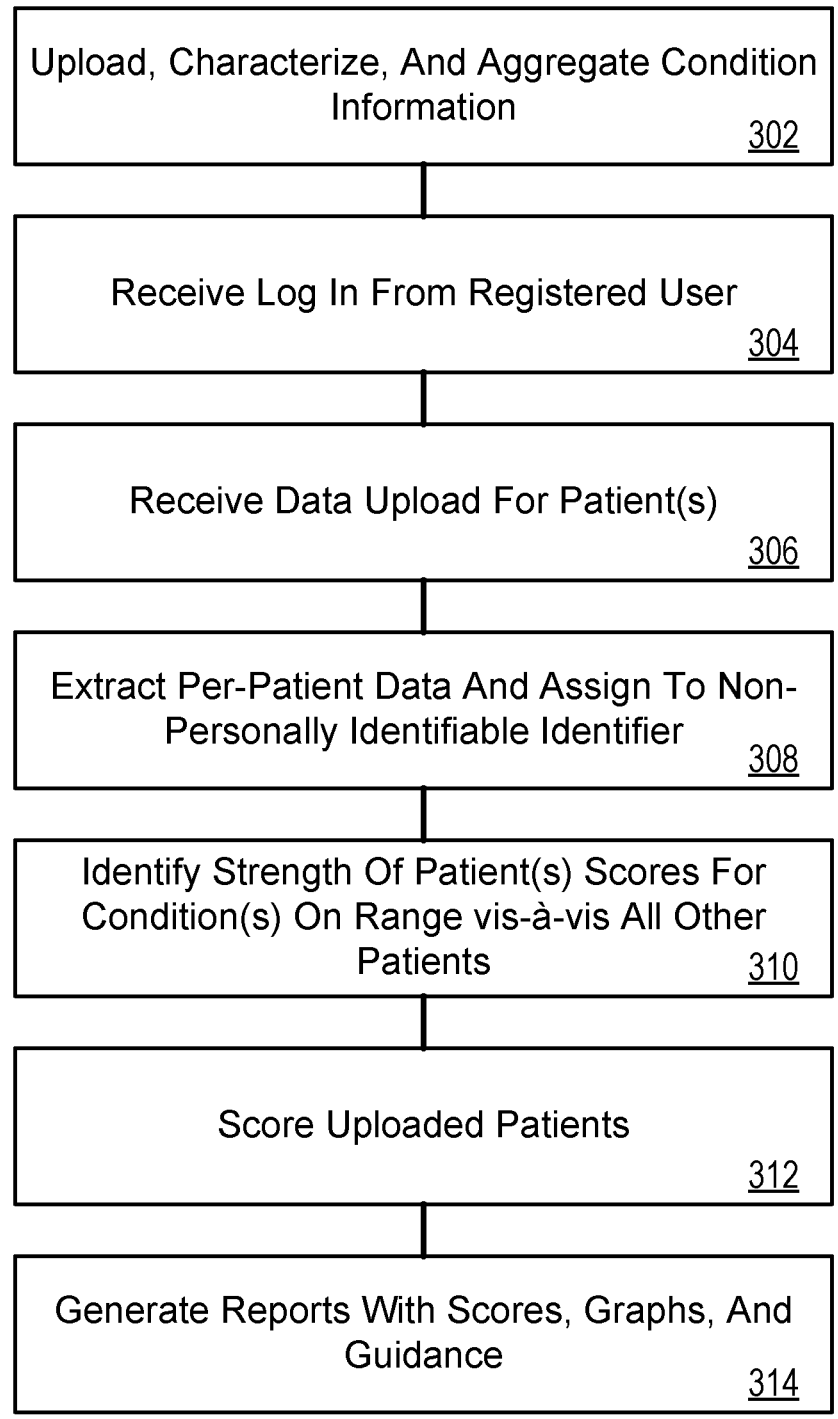
FIG. 3 is a flow chart of an example process for generating patient-specific comparative data.

FIG. 3 is a flow chart of an example process for generating patient-specific comparative data. In general, the process involves repeatedly receiving patient data and adding it to a running database, while also generating information that shows how the particular patient compares to aggregated data for the group in the database for a variety of different conditions.

The process begins at box 302, where a system receives an upload of condition information for one or more patients, and characterizes and aggregates the information. For example, the upload may occur by a user entering data into cells in a form or presenting data in a predefined format. The characterization and aggregation may involve applying predetermined processes to the uploaded data to transform the data and to create derivative data that can be used for subsequent comparison and other analysis as described above and below. Such information serves as the database against which future data for particular patients can be compared, and the submission of such data may be essentially continuous—i.e., each additional patient whose data is added may be combined into the overall database to make the comparison set even larger and more complete. Also, data for a particular patient may be entered multiple times, such as by initially entering data for a first sub-set of analytes, and subsequently adding data for a second sub-set of analytes, where an all conditions tool may provide reports with greater information in them after the subsequent upload of data occurs.

At box 304, the system receives a log in from a particular user who is registered with the system, such as from a lab assistant. The requirement for registration may help to ensure that the data that is uploaded to the system is properly obtained and represents the appropriate parameters of the patient in a manner defined by the system—so that the data in the system is not corrupted. Users may also need to be registered if the system charges for access to help defray the cost of providing such services to users.

At box 306, the system receives an upload of data characterizing one or more new patients (or new (additional or replacement) data for previously—identified patients). The data may have been gathered using an automatic testing system, and may characterize the patient data in a predefined matter. The data may be passed, for example, as an XML file, a CSV file, HTTP data from a web form, or other such mechanisms.

At box 308, per-patient data is extracted from the upload and is assigned a non-personally-identifiable identifier. Specifically, where data for a batch of patients is uploaded, each such patient may be given an ID number that is used to track them through the system, but that is incapable of allowing an operator of the system from actually identifying the patient. For example, a system may simply give each subsequent enrolled patient a next in a sequence of ID numbers. If later data is uploaded for the patient, the lab for the patient may provide the number to the system so that the system can correlate the old data and the new data.

At box 310, scores may be generated for the patient or patients with respect to a condition or conditions that the patient's data corresponds to. The score or scores may be generated as a comparative score to the scores of other patients previously uploaded for that condition or conditions. For example, the scores may range from 300 to 850 for a particular type of unit, and particular values of that unit may have been collected for a large and statistically significant number of patients (e.g., more than 1000 patients). Those values may be scaled as percentiles along a 1 to 100 percentile range, and newly added patients may be characterized in this step by their relative position in the percentile range. The position of the particular patient may also be compared to statistical ranges for patients with a condition, normal patients, or both. In performing such comparison, raw values for the analytes supplied by the user may be employed, or derivative values may be employed, such as by combining two or more analyte values according to a formula and a weighting function that is preprogrammed in the system.

At box 312, additional scores are generated for the uploaded patients. For example, additional percentile ranks may be generated for other conditions, and derivative scores may also be generated. For example, co-variance scores may be generated that compare the scores of a patient as between two different conditions that are represented by the raw data. In generating such scores, the system may identify which parameters (e.g., analytes) it received input for and may generate only scores for conditions that can be characterized adequately by those parameters. From such determination, a series of scores—one for each condition that can be scored—may be presented to a caregiver such as indicated below.

Finally, at box 312, one or more reports (whether textual, graphical, or a combination of the two) may be generated for providing to the user who uploaded the data for the patient or patients. Such reports may take the form of graphs shown in FIGS. 4A and 4C-4E discussed next.

FIG. 4A is a screen shot of an interface for presenting comparative patient data for two conditions requiring differential diagnosis. In this example of the graph 400, scores for a first condition are plotted along an x-axis 402, and scores for another condition are plotted along a y-axis 404. The score in each axis is calculated according to rules that consider any possible difference between the condition ranges of each analyte, and increase the score for condition 1 on the x-axis and for condition 2 in the y-axis. At the same time, the reverse process is applied to penalize the other condition. Each dot (e.g., 406) in the graph represents a particular patient, and appears at the relevant location on the graph for the parameters that were submitted for that patient. In this example, the two conditions are almost completely resolved from each other, so that a user can attribute a location on the top left quadrant to condition 2, and to the bottom right quadrant to condition 1. Top right locations are indeterminate, while lower left positions correspond to lack of correlation to either condition. The particular patient who is being analyzed is shown by a dot 408, which is positioned solidly in the bottom right quadrant, and thus corresponds to the condition assigned to the bottom right quadrant. Such information may be informative to a physician who is trying to decide whether the patient is affected with either one or the other condition.

FIG. 4B is a screen shot of an interface for selecting files containing patient data for post-analytical analysis. The interface may be accessed from a main menu system for a web site by a registered user who seeks to upload data that is stored in a particular form of file, such as a .csv file. Such a user may have created the file using a macro or other application at the user's site, where the application is programmed to format the data according to an API for the system that is to receive and analyze such data. In the figure is shown an interactive form by which a user can select a particular tool to be run (e.g., where each tool may be directed to a particular condition or combination of conditions, or to all possible conditions that can be analyzed given the data that the user inputs) The form also allows a user to identify a file (e.g., on the user's computer desktop) from which data is to be imported by the server-based system, where the user can also specify a subset of the file by identifying a range of cells in a spreadsheet that contain the relevant data. The user may then select to "run tools" on such data. Upon the user making such a selection, the data may be compared to the data for other patients in the database, and may subsequently be added to the database.

FIG. 4C is a screen shot showing a summary of an import of a file containing patient data. Such information appears below the display of FIG. 48. The summary in this example indicates each of the tools that were able to be run against particular possible conditions, and shows both scores for those conditions and interpretive text for s those scores— e.g., that the score represents the possibility or likelihood of a condition in the subject patient. The report includes interpretation guidelines that are customized for each condition and may suggest appropriate follow up tests.

FIG. 4D is a screen shot of a reporting tool for all conditions in a particular patient. In a top zone the tool indicates the types of conditions being analyzed along with other parameters, including the manner in which the scores are expressed. A "click to show analytes" selection, when selected, causes the display to expand and to show a list of all analytes that were submitted for the particular patient who is under consideration. This is also the window where data could be entered manually for a patient under test.

Lower portions of the report show the patient's score for each condition as a percentile rank against all patients known to have that condition, Below that, the whole set of scores is plotted. Thus, a quick visual review of the two plots can indicate that the patient is well within a range of other patients who have the condition or at or outside an edge of the range. Where the patient is an edge case so that the report is indeterminate, the user can plot a dual scatter plot as shown in FIG. 4A, or can select some part of the interface that displays data for the particular condition, which can lead to the display of FIG. 4E being shown, or select a 2nd tier test to improve both sensitivity and specificity.

In FIG. 4D, the conditions are sorted (left to right) according to the patient's closest correlation with other patients who have the particular condition. Thus, the left edge of the report will show the conditions that require greatest attention from an attending physician, while those to the right are conclusively not informative. Also, a key is provided at the bottom to indicate percentile ranges that correspond to the color that the icon for the particular patient will take for each of the particular conditions (depending on where the patient falls in the range relative to other patients).

FIG. 4E is a screen shot of a reporting tool for one patient condition. As noted, such a display may be generated by a user running a report on a single condition, or a user running a report on all conditions, and then clicking on the area of such an all conditions report, in an area associated with the particular single condition. In this instance, the particular condition is 2MBG, an inherited condition that involves a deficiency that prevents a patient from breaking down a certain branched chain amino acid. At the top of the report are certain numerical comparisons between the patient's values for certain conditions, and the values for other patients, such as other patients who are affected with this particular condition. Below that is shown graphical plots of values for different analytes that affect the condition, plotted as multiples of the normal median against a logarhythmic scale, with ranges being shown for both reference population and the condition under test, and the particular patient's value shown as a point relative to them. Below that are shown plots of particular values for different subsets of the total number of true positive cases with the condition.

At the left, is shown a score for the patient for the particular condition. The score can be normalized, such as to a 100 point scale, and may provide a more compact representation of where the patient sits with respect to the condition. A user-selectable link may also be provided to cause a display that shows the actual computation that led to any of the scores shown in this display, including where the values for the analytes enter the equation or equations and rules that are designed to prevent cross-talking among tools.

Thus, using the interfaces of FIGS. 4C and 4D, a registered user can see an overview of a patient's condition across a number of conditions, and can then choose to drill down and obtain detail about any particular condition. The user can be shown the patient's values relative to the values of others who have been determined to have the condition, and can be shown the patient's percentile value relative to such other patients. In such a manner, the user can be given extensive amounts of readily understandable information about the patient, and can thus make a quick but nuanced decision about the diagnosis to be provided to the patient.

Example

In one example, a population study was performed that included a first specimen of subjects born in Minnesota and California. The following exclusion criteria were chosen for both cohorts to minimize interfering variables: 1) birth weight<1800 g (N=2,214); 2) birth weight>1800 g and age at collection<24 hours (N=10); 3) birth weight>1800 g and age at collection>7 days (N=1,629). Current practice in California is to assign profiles not completely normal to one of three categories: out of range, review, and presumptive positive. Out of range indicates a single result exceeding the corresponding cutoff value. These findings are considered clinically insignificant, but a report is generated and sent to the primary care provider. Review status is triggered by multiple abnormalities. In most instances the resolution is like the out of range category, and a report is generated accordingly. Otherwise a review case is considered a presumptive positive and follow-up is initiated.

TABLE 1

Table 1 - Characteristics of the two population cohorts and analytical parameters

|  | Minnesota | California |
| --- | --- | --- |
| Period | Jan. 1, 2011 to Dec. 31, 2012 | Jan. 1, 2012 to Jun. 30, 2012 |
| Size of cohort | 141,228 | 177,174 |
| Source of reagents | Laboratory developed test | Commercial kit |
| Derivatization method | Butylation | No derivatization |
| Amino acids measured [b] | 18 | 13 |
| Amino acid ratios calculated [b] | 28 | 23 |
| Acylcarnitine measured [b] | 35 | 28 |
| Acylcarnitine ratios measured [b] | 39 | 38 |
| Active cutoff values [c] | 162 | 45 |
| % within R4S validation criteria | 40% | 22% |

[b] Individual amino acid and acylcarnitine species were included in overall counts only when all five reference percentile values (1%, 10%, 50%, 90%, and 99% ile) had been uploaded in R4S.
[c] Counts include both high and low cutoff values uploaded as of Oct. 31, 2013.

MS/MS Methods:

In Minnesota, newborn screening by MS/MS, the counts of analytes, calculated ratios, and active cutoff values is shown for both programs in Table 1. Second tier tests (2TT) include the following assays: 1) homocysteine, methylmalonic acid and methylcitric acid; 10-11 2) allo-isoleucine; 12 3) 3-hydroxyglutaric, glutaric acid, and ethylmalonic acid. California has adopted an underivatized method based on a commercial kit (STEPONE Newborn Screening, from Perkin Elmer, of Waltham, Mass.), and currently does not perform any second tier tests.

R4S Data and Tools:

As of Oct. 31, 2013, the true positive database included 16,059 newborns, identified according to local protocols and/or professional guidelines, corresponding to 1,115,543 data points. Fifty-six common tools are available together with 173 site-specific copies and 17 dual scatter plots for differential diagnosis purposes.

The tool runner tool of the RS4 system calculates simultaneously a score for all available tools for each case within a batch that is uploaded to the website as a comma separated value (.csv) file void of any patient health information. Analyte results are paired with the corresponding logical observation identifiers names and codes code. Processing was completed in seconds and generated an interactive tabular report of any informative score. The all condition tool generates an interactive graphic report of all scores, including zeros, for one case at the time. Both types of report are linked to each individual tool.

Results:

Current Status and Validation Criteria of Cutoff Values

Figure 4F:
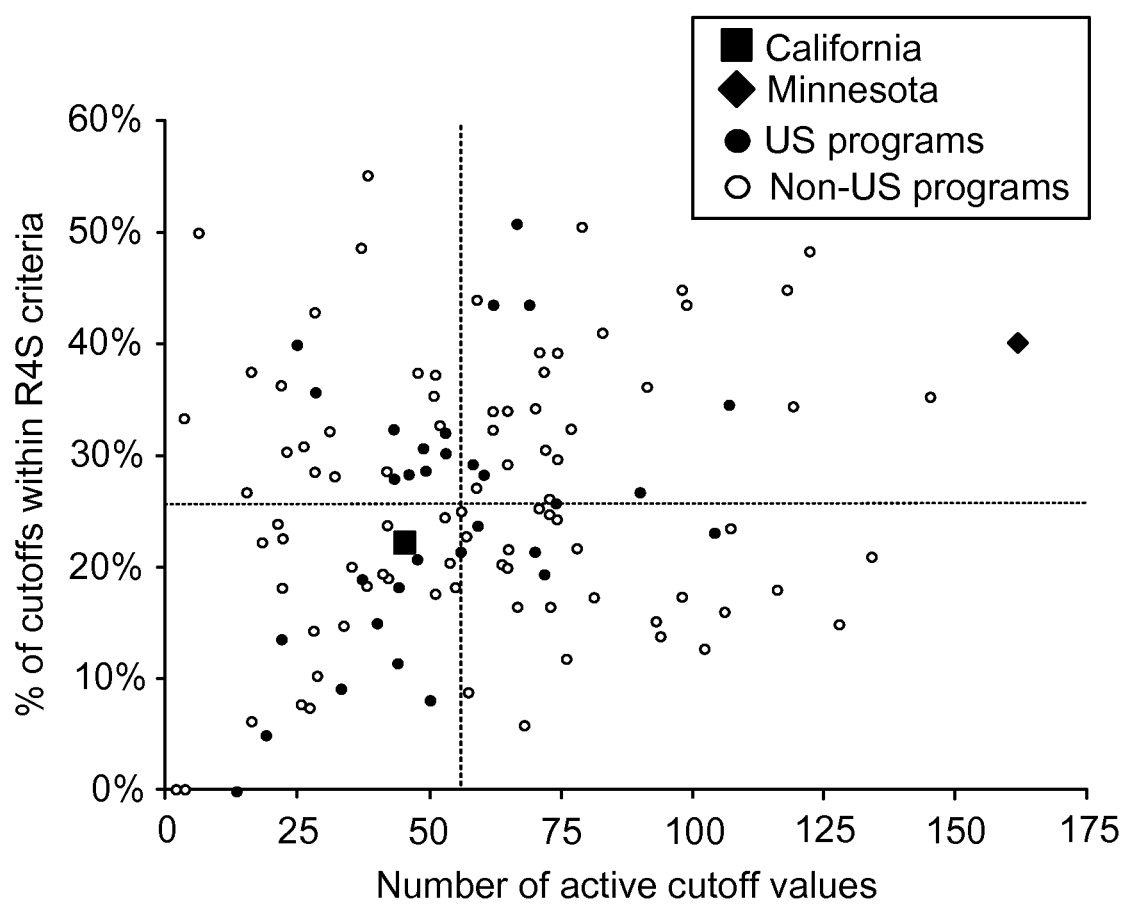
FIG. 4F is a plot of Minnesota and California cohort data.

To establish a baseline for the comparison between performance outcomes, the size and adequacy of the cutoff panels of the two programs were compared to those of all participating sites in R4S. FIG. 4F shows the number of cutoff values plotted versus the proportion that meets the validation criteria. Minnesota relies on the largest complement of cutoff values among R4S sites, and the proportion within the validation criteria is well above the median of all sites. California is slightly below the median for both parameters.

Retrospective Analysis Using the Tool Runner

Figure 4G:
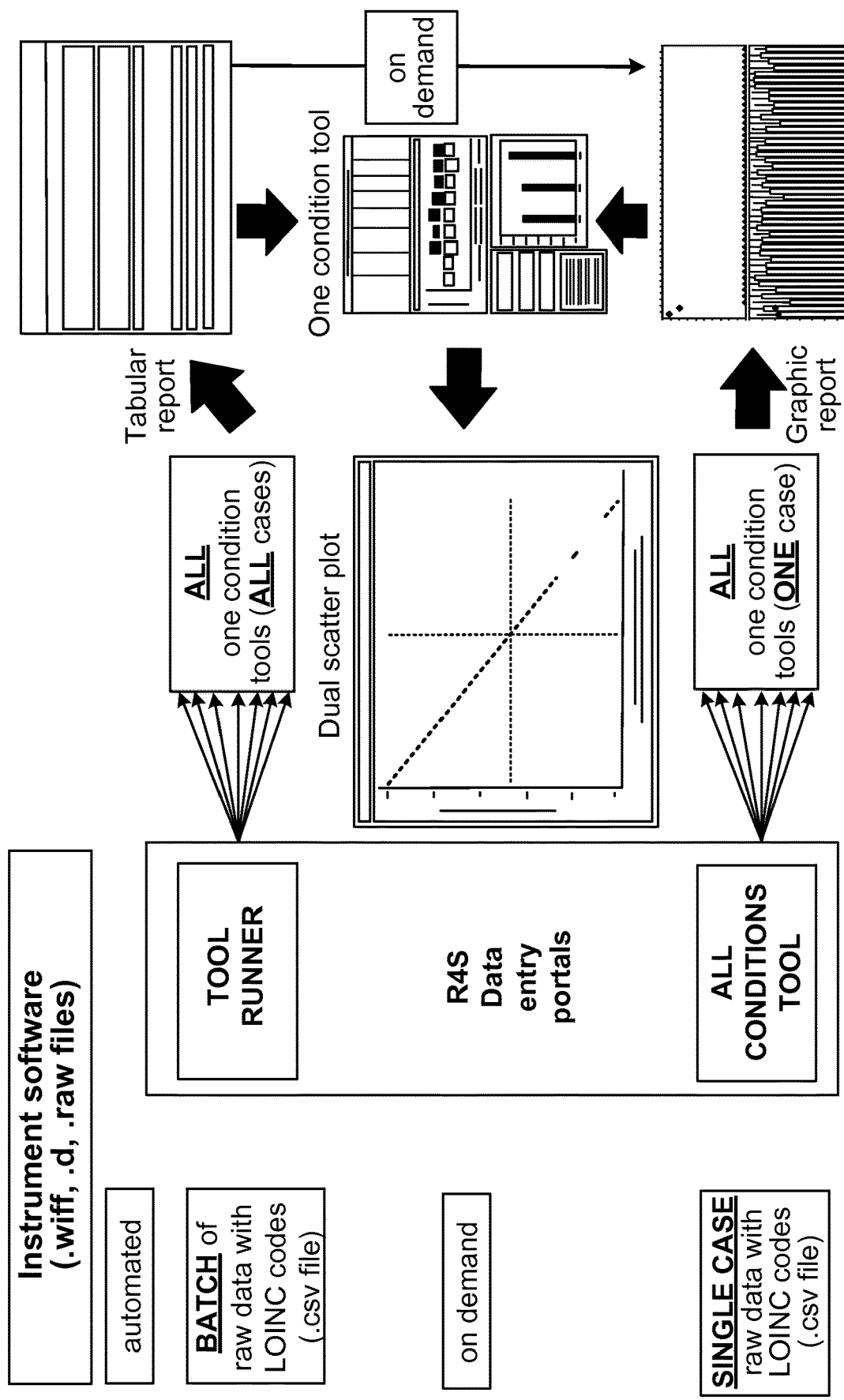
FIG. 4G is a schematic diagram showing the interaction of components described herein.

FIG. 4G summarizes how MS/MS data are converted to a report using the tool runner application (components of which are discussed in more detail with respect to certain figures above): a .csv file is uploaded to the R4S website, all one condition tools are run simultaneously and a summary report of informative scores is produced. A 96-well plate includes approximately 90 patient samples, the number of results and ranges from 10,800 in Minnesota to 9,180 in California.

Retrospective Comparison of Minnesota Population

The Minnesota population study was included in 2,270 plates. Results were reviewed in chronological order to create a cumulative database of the findings summarized in Table 2. There were almost 40,000 instances of results either above or below a given cutoff value. Most of them were deemed to be irrelevant and overruled, but to do so a visual inspection of the profile and of the demographic information was required, a process that is prone to inconsistency because of the subjectivity and diverse level of experience of individuals performing the evaluation. The utilization rate of 2TT was 1 in 81 specimens. Cases of Hmong ethnicity affected with 2-methylbutyryl-CoA dehydrogenase deficiency were not included in the count of true positive cases. 15-16

TABLE 2

Comparison between cutoff-based system and R4S post-analytical interpretive tools in Minnesota

|  | Minnesota | |
| --- | --- | --- |
|  | Cutoff values | R4S Tools |
| Abnormal amino acid results | 7,911 | 1,407 |
| Abnormal amino acid ratio results | 6,235 |  |
| Abnormal acylcarnitine results | 18,216 | 1,144 |
| Abnormal acylcarnitine ratio results | 8,393 |  |
| Total abnormal results/informative tools | 39,845 | 2,551 |
| Cases reflexed to 2nd tier tests | 1,734 | 1,257 |
| True negative cases | 141,092 | 141,138 |
| False positive cases [a] | 84 | 39 |
| True positive cases [b] | 52 | 51 |
| False negative cases [c] | 0 | 1 |

[a] Abnormal findings based on cutoff system that resulted in a referral to follow-up of a false positive case- Amino acids (count): citrulline high (3), citrulline low (3), isoleucine-leucine (1), methionine high (3), and phenylalanine high (2); Acylcarnitines: free carnitine high (1), free carnitine low (13), propionylcarnitine (1), butyryl-isobutyrylcarnitine (22), methylmalonyl-succinylcarnitine (1), glutarylcarnitine (1), hydroxyl-isovalerylcarnitine (21), octanoylcarnitine (1), decadienoylcarnitine (1), tetradecenoylcarnitine (8), and hydroxyl-hexadecanoylcarnitine (2).
[b] Amino acid disorders: Argininosuccinic acidemia (1), Disorder of biopterin regeneration (1), carbamylphosphate synthase deficiency (1), phenylalanine hydroxylase deficiency (benign) (6), maple syrup urine disease (1), ornithine transcarbamylase deficiency (1), and phenylalanine hydroxylase deficiency (classic) (6); Fatty acid oxidation disorders: maternal carnitine deficiency (7), long-chain L-3-hydroxy acyl-CoA dehydrogenase deficiency/trifunctional protein deficiency (2), medium-chain acyl-CoA dehydrogenase deficiency (4), short-chain acyl-CoA dehydrogenase deficiency (1), and very-long chain acyl-CoA dehydrogenase deficiency (5); Organic acid disorders: 3-methylcrotonyl-CoA carboxylase deficiency (1), maternal 3-methylcrotonyl-CoA carboxylase deficiency (1), maternal 3-methylglutaconyl-CoA hydratase deficiency (1), maternal vitamin B12 deficiency (6), glutamate formiminotransferase deficiency (1), glutaryl-CoA dehydrogenase deficiency (1), maternal glutaryl-CoA dehydrogenase deficiency (1), isobutyryl-CoA dehydrogenase deficiency (2), isovaleryl-CoA dehydrogenase deficiency (1), transcobalamin receptor defect (1).

For the comparison study, .csv files were uploaded to the tool runner. After all reports were combined, there were only 2,551 cases with one or more informative scores and approximately half of them would have been reflexed to a 2TT, a reduction in utilization by 42% to 1 in 115 specimens (Table 2). The primary findings that resulted into a referral to follow-up of newborns later resolved as FP cases, and the underlying conditions of the true positive cases are listed in the legend of Table 2. The most notable reductions of FPs were related to acylcarnitine species: seven of eight FP cases caused by elevated concentration of tetradecenoylcarnitine, the primary marker of very long-chain acyl-CoA dehydrogenase deficiency, were categorized by the dual scatter plot as likely heterozygotes (five were confirmed by molecular analysis), an interpretation that could have prevented their referral to follow-up; ten of 22 cases with elevated isobutyryl-butyrylcarnitine had no informative scores for all four conditions related to this analyte, including seven cases who carry one or two copies of common polymorphic variants 17-19 and one copy of either a pathogenic mutation or a variant of unknown significance. Nine of the remaining 12 cases (three confirmed carriers of pathogenic mutations) had a score of zero using the tool based on the disease ranges of cases with two pathogenic mutations of the short-chain acyl-CoA dehydrogenase gene. These cases were still counted as residual FPs because of either elevated concentration of ethylmalonic acid by 2TT or because of the possibility of a different underlying diagnosis. Finally, eight of the 21 cases with elevated hydroxy-isovalerylcarnitine had no informative scores for all six conditions related to this analyte. On the amino acid side, four referrals could have been prevented by an informative score of the total parenteral nutrition (TPN) tool.

With one exception, all true positive cases were identified correctly by the tools. The missed case was a newborn with trifunctional protein deficiency, his older sibling was diagnosed by newborn screening. After C-section delivery the newborn was placed immediately on a frequent feeding regimen, the specimen was collected at 29 hours of age. The acylcarnitine profile showed hydroxy-hexadecanoylcarnitine slightly above the cutoff value (0.20 nmol/mL, cutoff: 0.15). The tool score was below the threshold defined by the first percentile of all scores available at the time of testing (N=70). The two FP cases triggered by the same analyte did not produce an informative score and could have been prevented.

Retrospective Comparison of California Population

The outcome of this cohort is summarized in Table 3. Instead of a count of results exceeding cutoff values, this cohort was sorted in separate batches based on actual outcome. In the true negative group, 2,422 cases (1.5%) presented with at least one informative score. Because California relies on a network of 15 metabolic referral centers that would likely become aware of any case missed by newborn screening, the following analysis is based on the assumption that there were no additional false negative events during the period under evaluation. Table 3 shows the relative proportions which could have been resolved conclusively as true negatives on the basis of either a TPN score or by reflexing to a 2TT, particularly homocysteine measurement in a large number of cases with a concentration of methionine below the chosen cutoff value. For the remaining cases, an expanded analyte panel could have prevented the generation of 20% of the residual scores, in particular the addition of argininosuccinic acid, glutamic acid and glutamine, the latter two for better interpretation of cases with a low concentration of citrulline.

Another avenue of potential resolution could have been verification of an abnormal finding by using a derivatized method, particularly to mitigate the frequent flagging of malonylcarnitine due to either isobaric interference in the underivatized method or the choice of internal standard.26 Another 20% of the residual scores could have been overruled using interpretation rules. For example, the cumulative experience in R4S with carnitine uptake defect (N=325) and related maternal cases 1, 27-28 (N=162) has shown that a borderline concentration of free carnitine could be disregarded when the sum of propionylcarnitine and palmitoylcarnitine is >2 nmol/mL. The last 645 cases were reconciled as true negative outcomes because recalculation of the score after switching to-site specific reference percentiles turned the score to a 0% ile rank, i.e. a score lower than the lowest known true positive case detected in California. 83% of out-of-range and review cases could have been prevented completely by combining lack of informative scores and TPN scores. 2TT could have resolved more than 500 additional cases.

Table 3 shows the distribution of the remaining cases according to the same criteria applied to the true negative

TABLE 3

Comparison between cutoff-based system and R4S post-analytical interpretive tools in California

| Case resolution based on cutoff values (% of cohort) | Cutoff values | R4S Tools | |
|---|---|---|---|
| NEGATIVE (94.3%) | | | |
| No informative scores (%) | 166,118 | 163,696 | (98.5%) |
| Informative score for TPN | | 343 | (0.2%) |
| Scores likely to be overruled by a $2^{nd}$ tier test | | 801 | (0.5%) |
| Resolution likely to be improved by adding markers | | 271 | (0.2%) |
| Potential resolution by derivatized method | | 125 | (0.1%) |
| Scores overruled by proven interpretation rules | | 237 | (0.1%) |
| Scores overruled by site-specific tools | | 645 | (0.4%) |
| OUT OF RANGE & REVIEW (5.4%) | | | |
| No informative scores (% of total) | 9,561 | 6,285 | (65.7%) |
| Informative score for TPN | | 1,663 | (17.4%) |
| Informative scores likely to be overruled by a $2^{nd}$ tier test | | 513 | (5.4%) |
| Resolution likely to be improved by adding markers | | 672 | (7.0%) |
| Potential resolution by derivatized method | | 42 | (0.4%) |
| Scores overruled by interpretation rules | | 36 | (0.4%) |
| Scores overruled by site-specific tools | | 350 | (3.7%) |
| FALSE POSITIVES (0.3%) | | | |
| No informative scores (% of total) | 454 [a] | 97 | (21.4%) |
| Informative score for TPN | | 68 | (15.0%) |
| Informative scores likely to be overruled by a $2^{nd}$ tier test | | 58 | (12.8%) |
| Carrier status assigned by dual scatter plot | | 6 | (1.3%) |
| Resolution likely to be improved by adding markers | | 43 | (9.5%) |
| Potential resolution by derivatized method | | 7 | (1.5%) |
| Scores overruled by interpretation rules | | 128 | (28.2%) |
| Confirmed maternal cases | | 7 | (1.5%) |
| Residual false positive cases | | 40 [b] | (8.8%) |
| TRUE POSITIVES (0.03%) | | | |
| No informative scores (% of total) | 43 [c] | 1 | (2.0%) |
| Informative scores likely to be confirmed by a $2^{nd}$ tier test | | 7 | (36.0%) |
| Scores supported by interpretation rules | | 4 | (8.0%) |
| Correctly identified true positive cases | | 42 | (98.0%) |
| FALSE NEGATIVES (0.001%) | | | |
| No informative scores (% of total) | 2 | 1 | (50.0%) |
| Improvable detection by adding markers | | 2 | (n/a) |
| Potentially avoided false negative cases | | 1 | (50.0%) |

[a] Abnormal findings based on cutoff system that resulted in a referral to follow-up of a false positive case- Amino acids (count): citrulline high (7), citrulline low (62), isoleucine-leucine (12), methionine high (22), methionine low (20), ornithine high (1), and phenylalanine high (12); Acylcarnitines: free carnitine low (149), propionylcarnitine (16), butyryl-isobutyrylcarnitine (9), isovaleryl-2-methylbutyrylcarnitine (8), glutarylcarnitine (60), hydroxyl-isovalerylcarnitine (15), octanoylcarnitine (8), malonylcarnitine (14), tetradecenoylcarnitine (8), hexadecanoylcarnitine (2).
[b] Abnormal findings based on R4S tools that still would have resulted in a referral to follow-up of a false positive case- Amino acids (count): citrulline high (1), citrulline low (0), isoleucine-leucine (0), methionine high (0), methionine low (0), ornithine high (1), and phenylalanine high (1); Acylcarnitines: free carnitine low (23), propionylcarnitine (0), butyryl-isobutyrylcarnitine (0), isovaleryl-2-methylbutyrylcarnitine (0), glutarylcarnitine (0), hydroxyl-isovalerylcarnitine (10), octanoylcarnitine (1), malonylcarnitine (0), tetradecenoylcarnitine (3), and hexadecanoylcarnitine (0).
[c] Amino acid disorders: citrullinemia type 1 (3), maple syrup urine disease (1), ornithine transcarbamylase deficiency (2), disorder of biopterin biosynthesis (1), phenylalanine hydroxylase deficiency (benign) (6), and phenylalanine hydroxylase deficiency (classic) (9); Fatty acid oxidation disorders: carnitine uptake defect (3), medium-chain acyl-CoA dehydrogenase deficiency (4), short-chain acyl-CoA dehydrogenase deficiency (2), and very-long chain acyl-CoA dehydrogenase deficiency (1); Organic acid disorders: 3-methylcrotonyl-CoA carboxylase deficiency (6), isobutyryl-CoA dehydrogenase deficiency (2), isovaleryl-CoA dehydrogenase deficiency (1), methylmalonic acidemia (2).

cases. During the time period of this study, there were 454 cases reported as presumptive positives that were later reclassified as FPs. Again, 40% of them could have been prevented by combining either lack of informative scores or a score indicative of TPN. Another 17% could have been resolved by a 2TT, with an estimated utilization rate of 1 in 128 samples. For the remaining cases, the same criteria listed above for the other categories could have reduced significantly the number of presumptive positives where a referral to follow-up was made. In a best case scenario, the residual number of FPs could have been reduced below 10% of the initial count. With one exception, a case confirmed to be affected with ornithine transcarbamylase deficiency, all true positive cases were correctly identified.

One of two known false negative cases, both affected with ornithine transcarbamylase deficiency, could have been detected by the site specific tool for that condition, and the resolution of both could have been aided by the measurement of glutamate and glutamine.

Table 4 shows a comparison between actual and estimated performance metrics, the outcome in the two cohorts was essentially the same after application of the interpretive tools. The most notable improvements were observed in terms of positive predictive value and particularly FP rate. These outcomes are comparable to findings that have been reported by other programs: a similarly designed comparative study applied to more than 180,000 Swedish newborns reduced the FP rate from 0.07% to 0.05%. In another comparative study of 96,000 newborns in central Italy, the FP rate declined from 2.3% to 0.6%.

TABLE 4

Comparison of performance metrics between cutoff-based systems (actual) and R4S post-analytical interpretive tools (estimated) in Minnesota and California

| Performance metrics | Minnesota | | California | |
| --- | --- | --- | --- | --- |
| | Cutoff values (actual) | R4S tools (estimated) | Cutoff values (actual) | R4S tools (estimated) |
| Sensitivity | 100.0% | 98% | 96% | 98% |
| Positive predictive value | 38% | 57% | 10% | 52% |
| Specificity | 99.94% | 99.97% | 99.74% | 99.97% |
| False positive rate | 0.06% | 0.03% | 0.26% | 0.03% |

Finally, a transition to the R4S tools as the primary mode of post-analytical interpretation in Minnesota for 2013 (January-October) has resulted in further performance improvement: among 59,481 newborns tested, 25 of 40 cases with abnormal MS/MS results who were referred to follow-up were later confirmed to be true positive cases, the preliminary annual positive predictive value and FP rate are 63% and 0.025%, respectively. Since November 2011 the tool runner has been used 17,202 times by 21 program worldwide, corresponding to 62 million calculated scores.

Figure 5:
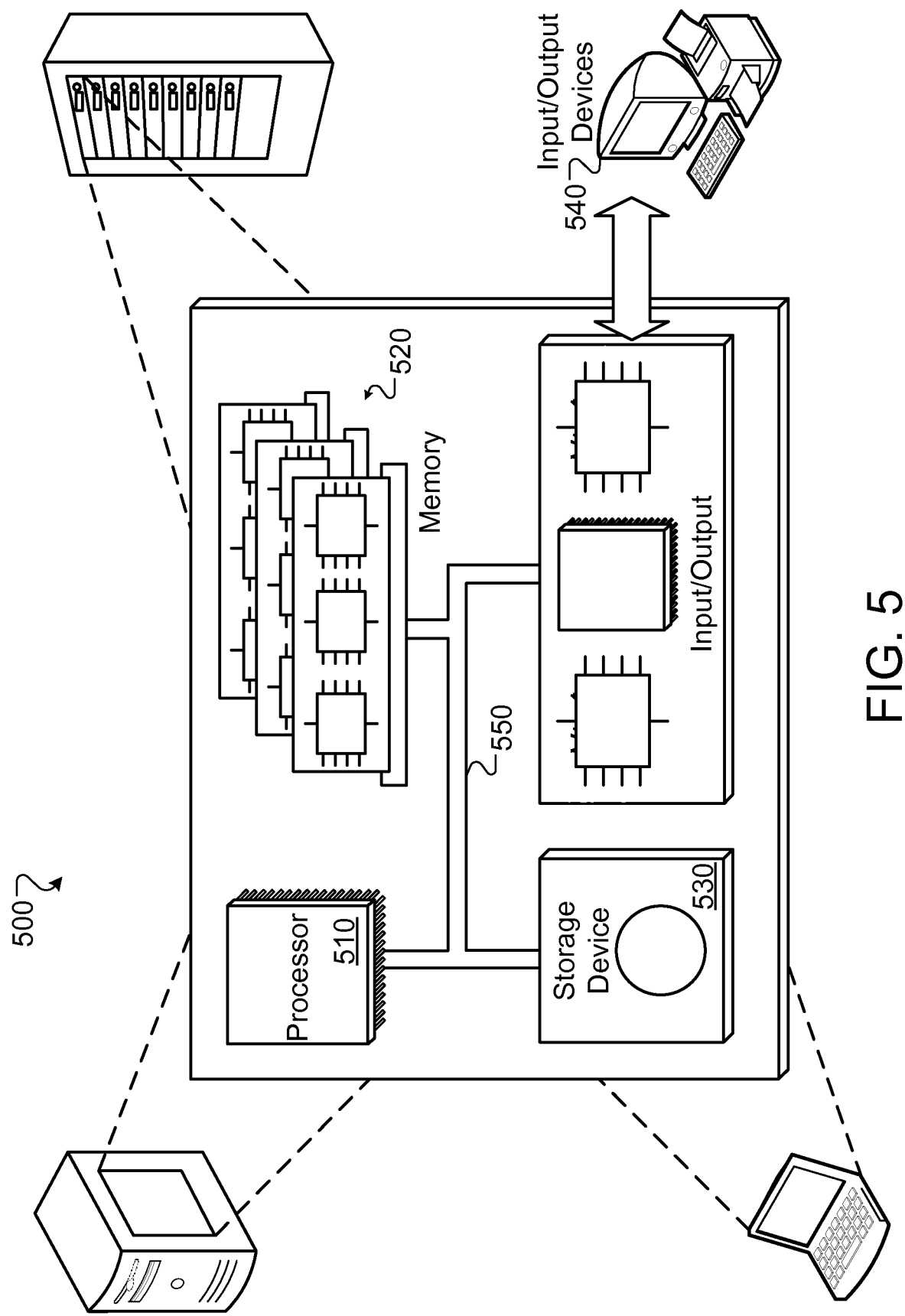
FIG. 5 shows a general computer system that can provide for management and control of electrical energy delivery to a data center.

FIG. 5 shows a general computer system 500 that can provide for computing techniques as described above. For example, with respect to the techniques discussed above, the system 500 can be used to operate software executing a control system for coordinating the action of computer servers in a computer data center, power supplies for the computer servers, and power generation units like those discussed above, along with more central components. For example, computer servers may estimate their electrical needs for the near future and may each inform their corresponding power supply (i.e. that power supply that serves them with electricity). The power supplies may in turn communicate with each other over a data network, and/or with a generation unit that serves electricity to them. Such communications may cause the generation unit to "power up" to meet the coming demand, or to ration energy supplied to other computer servers in the domain served by the particular generation unit. In turn, the generation units may communicate to a central control system, such as to have the central control system open or close one or more valves so that an adequate amount of natural gas or other fluid is provided to meet the demand of particular generation units that may be distributed relatively evenly throughout the data center facility. Each of these active communicating components may include computing components like those discussed here for system 500.

The system 500 may, for example, control the switching of power and the delivery through different domains in the system, such as in the manner discussed for FIG. 5 above. The system 500 may exemplify computers located at each power supply in a system, computers that communicate with and control the power used by and the activities of such power supplies, and other computers that communicate via a network, including a central computer system that controls and coordinates power distribution throughout a computer data center facility or facilities and between different computer data center facilities.

The system 500 may be implemented in various forms of digital computers, including personal digital assistants, tablets, and other appropriate computers. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 500 includes a processor 510, a memory 520, a storage device 530, and an input/output device 540. Each of the components 510, 520, 530, and 540 are interconnected using a system bus 550. The processor 510 is capable of processing instructions for execution within the system 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the system 500. In one implementation, the storage device 530 is a computer-readable medium. In various different implementations, the storage device 530 may be a floppy disk device, a hard disk device, an optical disk device, or a tape device.

The input/output device 540 provides input/output operations for the system 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described may be employed, and may be encompassed by the following claims.

What is claimed is:

1. A computer-implemented method for identifying a status of a particular patient with respect to multiple medical conditions, the method comprising:

generating, with a computer system, an electronic data model that aggregates information from analytes for a population of tens of thousands of patients treated across multiple different healthcare systems and indicative of a plurality of medical conditions for particular ones of the population of patients that are common across the population of patients, the model trained by remote representatives from multiple different distributed healthcare systems adding analyte information for particular ones of their patients;

providing, with the computer system, a public computer portal through which the remote representatives from multiple different distributed healthcare systems are enabled to upload data for their patients, wherein the uploaded data is added to the data that aggregates, and in return for uploading the data for their patients, the representatives are provided data for displays indicating health of their respective patients;

receiving, via upload through the computer portal, data that characterizes analytes from the particular patient that are potentially indicative of presence or absence of at least a plurality of different medical conditions;

training the electronic data model by sequentially adding to the electronic data model data about analytes for additional particular patients, and arranging the resulting electronic data model including data for tens of thousands of patients for comparison to values for future particular patients;

producing for the particular patient and from the received data, (a) a value for a first condition indicated by a first plurality of analytes from the particular patient, (b) a value for a second condition indicated by a second plurality of analytes from the particular patient;

producing a statistical range or distribution for each of the first and second conditions for analytes for members of the population of patients;

generating graphical display data, with the server system, that displays a graph that indicates, on a first axis, the value of the first condition for the particular patient relative to the statistical range or distribution for members of the population of patients, and concurrently on a second axis, the value of the second condition of the particular patient relative to the statistical range or distribution for members of the population of patients, so as to present a reference set of values that graphically presents co-variance for the particular patient relative to members of the population of patients for the first and second conditions, arranged for review by a caregiver in determining a diagnosis for a condition of the particular patient; and updating the electronic data model by adding data for conditions of the particular patient to a database that aggregates statuses of the plurality of patients, for conditions of the particular patient that are common to conditions of the plurality of patients, and making the updated electronic data model available for comparison to subsequently-uploaded data for other particular patients.

2. The computer-implemented method of claim 1, wherein the data that aggregates information from analytes for a population is analyzed using multivariate pattern recognition techniques.

3. The computer-implemented method of claim 1, wherein the data that graphs so as to present co-variance, graphs the particular patient positioned in relation to plotted locations for patients known to have been indicated to the computer system as having the first and second conditions.

4. The computer-implemented method of claim 1, wherein the data that characterizes analytes from the particular patient is expressed by data from laboratory markers.

5. The computer-implemented method of claim 1, wherein the data provided for review is formatted to present a scatter plot that shows positions of the particular patient among the members of the population of patients for the first and second conditions, wherein each axis of the scatter plot represents the likelihood of having a respective one of the first and second conditions.

6. The computer-implemented method of claim 1, further comprising receiving data from a registered user of the computer system, the data received from the registered user defining a tool developed by the registered user and for use by other users, for analyzing and expressing relative positions of patients with respect to a particular condition.

7. The computer-implemented method of claim 6, further comprising identifying that an administrator of the computer system has indicated that the tool is approved, and in response, making the tool available to other registered users of the computer system.

8. The computer-implemented method of claim 1, further comprising checking the received data that characterizes analytes from the particular patient at the time it is uploaded to confirm that the received data is within acceptable defined ranges.

9. The computer-implemented method of claim 1, wherein generating the graphical display data comprises identifying which conditions, of the plurality of conditions, are capable of being identified for the particular patient based on identifying analytes provided for the particular patient to the computer system.

10. One or more tangible computer-readable media having record thereon instructions that, when executed, perform operations comprising:
generating, with a computer system, an electronic data model that aggregates information from analytes for a population of tens of thousands of patients with respect to a plurality of medical conditions for particular ones of the population of patients that are common across the population of patients, the model trained by remote representatives from multiple different distributed healthcare systems adding analyte information for particular ones of their patients;
providing, with the computer system, a public computer portal through which the remote representatives from multiple different distributed healthcare systems are enabled to upload data for their patients, wherein the uploaded data is added to the data that aggregates, and in return, the representatives are provided data for displays indicating health of their respective patients;
receiving, via upload through the computer portal, data that characterizes the analytes from the particular patient that are potentially indicative of presence or absence of at least a plurality of different medical conditions;
training the electronic data model by sequentially adding to the electronic data model data about analytes for additional particular patients of population of patients and arranging the resulting electronic data model including tens of thousands of patients for comparison to values for the particular patient;
producing for the particular patient and from the received data, (a) a value for a first condition indicated by a first plurality of analytes for the particular patient, and (b) a value for a second condition indicated by a second plurality of analytes for the particular patient;
producing a statistical range or distribution for each of the first and second conditions for analytes for members of the population of patients;
generating graphical display data that displays a graph that indicates, on a first axis, the value of the first condition for the particular patient relative to the statistical range or distribution for members of the population of patients, and concurrently on a second axis, the value of the second condition of the particular patient relative to the statistical range or distribution for members of the population of patients, so as to graphically represent, with a computer display, a reference set of values that graphically presents co-variance for the particular patient relative to members of the population of patients for the first and second conditions arranged for review by the caregiver in determining a condition of the particular patient; and
updating the electronic data model by adding data for conditions of the particular patient to a database that aggregates statuses of the plurality of patients for conditions of the particular patient that are common to conditions of the plurality of patients, and making the updated electronic data model available for comparison to subsequently-uploaded data for other particular patients.

11. The tangible computer-readable media of claim 10, wherein the data that aggregates information from analytes for a population is analyzed using multivariate pattern recognition techniques.

12. The tangible computer-readable media of claim 10, wherein the data that graphs so as to present co-variance, graphs the particular patient positioned in relation to plotted locations for patients indicated to the computer system as having the first and second conditions.

13. The tangible computer-readable media of claim 10, wherein the data that characterizes the analytes from the particular patient is expressed by data from laboratory markers.

14. The tangible computer-readable media of claim 10, wherein the graphical representation is formatted to present a scatter plot that shows positions of the particular patient among the population of patients for the first and second conditions, wherein each axis of the scatter plot represents the likelihood of having a respective one of the first and second conditions.

15. The tangible computer-readable media of claim 10, wherein the operations further comprise receiving data from a registered user of the computer system, the data received from the registered user defining a tool for analyzing and expressing relative positions of patients with respect to a particular condition.

16. The tangible computer-readable media of claim 15, wherein the operations further comprise identifying that an administrator of the computer system has indicated that the tool is approved, and in response, making the tool available to other registered users of the computer system.

17. The tangible computer-readable media of claim 10, wherein generating the graphical display data comprises identifying which conditions, of the plurality of conditions, are capable of being identified for the particular patient based on identifying analytes provided for the particular patient to the computer system.

* * * * *